United States Patent [19]

Veenstra

[11] Patent Number: Plant 7,631

[45] Date of Patent: Aug. 27, 1991

[54] LILY PLANT NAMED 'BEAUDACIOUS'

[75] Inventor: Rien Veenstra, Wilsonville, Oreg.

[73] Assignee: Oregon Bulb Farms, Inc., Aurora, Oreg.

[21] Appl. No.: 513,484

[22] Filed: Apr. 23, 1990

[51] Int. Cl.[5] ..... A01H 5/00

[52] U.S. Cl. ..... Plt./68

[58] Field of Search ..... Plt./68, 87.4

*Primary Examiner*—Howard J. Locker

*Attorney, Agent, or Firm*—Charles W. Rummler

[57] ABSTRACT

A new variety of Asiatic hybrid lily plant of the chalice type particularly distinguished by its profuse production of medium size flowers having tepals of a generally orange buff color each bearing a ruby red brush mark extending from the top of the nectary for about 2 to 3 cm. towards the tepal center, the flowers being borne individually on generally upright pedicels carried in a more or less umbel arrangement adjacent the upper end of a strong, erect stem having a length of 110 to 120 cm., the flowers blooming annually and profusely during mid-season and having abundant foliage.

1 Drawing Sheet

BACKGROUND OF THE NEW PLANT

This Asiatic hybrid lily originated as a hybrid seedling produced at Sandy, Oreg. by crossing an unnamed and unpatented hybrid with pollen from the variety Endeavor, U.S. Plant Pat. No. 6,026, this particular seedling having been selected by me for propagation because of its very unusual orange buff primary flower coloration strongly marked in the inner half portion of each tepal to present a very striking and unusual appearance and asexual propagation of this seedling was done at Sandy, Oreg. by scaling and by tissue culture with such success that propagation in that manner was continued through several successive generations which demonstrated conclusively that the novel characteristic of the selected seedling would hold true from generation to generation and appeared to be firmly fixed. Propagation in this same manner is being done at Aurora, Oreg.

DESCRIPTION OF THE DRAWING

My new variety of Asiatic hybrid lily is illustrated by the accompanying full color photographic drawing which shows a three-quarter face view of a fully opened flower together with a number of buds in various stages of maturity, the color designations herein specified being reproduced as nearly truly as can be reasonably obtained by conventional photographic procedures.

DESCRIPTION OF THE NEW PLANT

The following is a detailed description of my new Asiatic lily plant as observed at Aurora, Oreg., with the color designations being according to The R.H.S. Color Chart published by The Royal Horticultural Society of London, England.

THE PLANT

Origin: Seedling.

Parentage:

*Seed parent.*—A hybrid originated by a cross of the variety Sterling Star by the variety Brink, neither of the stated varieties being patented.

*Pollen parent.*—The variety Endeavor, U.S. Plant Pat. No. 6,026.

Classification:

*Botanic.*—Division — 1A, UPR Asiatic hybrid lily.

*Commercial.*—Hybrid Lilium clone.

Form: Erect and stately single stem.

Height: About 110 to 120 cm.

Main stem length: 110 to 120 cm.

Growth: Vigorous, upright and very strong.

Foliage:

*Quantity.*—Abundant.

*Size of leaf.*—About 5 to 11 cm. long and about 3 to 3.5 cm. wide.

*Shape of leaf.*—Lanceolate with entire margins.

*Texture.*—Leathery.

*Appearance.*—Glossy.

*Color.*—Upper side — Dark Green. Under side — Somewhat lighter Green.

Bulbs:

*Size.*—Ranging to 25 cm. in circumference for commercial use.

*Color.*—White.

THE BUD

Shape: Long ovoid with obtuse apex.

Size: About 2 cm. in diameter and about 8 cm. long.

Rate of opening: The bud opens slowly at maturity in response to light.

Color:

*When tepals first divide.*—Orange Buff 26-D.

*When tepals begin to unfurl.*—Orange Buff 26-D.

Pedicel:

*Length.*—About 30 cm.

*Character.*—Erect and rigid.

*Color.*—Yellow Green 147-A.

THE FLOWER

Blooming habit: Annually and profusely during mid-season.

Size of flower: Medium.

*Diameter.*—About 14 to 16 cm.

Borne: In a raceme and somewhat umbel cluster at the top of the main stem.

Shape:

*When bloom first opens.*—Cup shaped.

*When bloom matures.*—Generally flat.

Tepalage:

*Number.*—Six.

*Arrangement.*—Hexagonal with inside tepals alternating above the outside tepals.

*Form.*—Elliptical with entire margins and acute apex.

*Texture.*—Leathery.

*Aspect.*—Satiny.

*Color.*—Outer tepals — body, Orange Buff 22-D with brush mark of Ruby Red 59-A at the top of the nectary furrow and extending about 2 to 3 cm. towards the tepal center with a width of about 1.5 cm. Base — Yellow Green 144-B. Reverse side — Orange Buff 22-C with tepal edge and tip of Yellow Ochre. Inside tepals — body, Yellow Orange 18-B marked with Red Purple 59-A at the top of the nectary furrow and numerous Ruby Red spots spread laterally from each side of the nectary to the tepal margins and for the length of the brush marks.

Discoloration after full bloom: The flower color becomes more orange and fades as the blossom ages.

Fragrance: None.

Persistence: The petals stay on the stem for approximately three weeks providing a long lasting quality for the bloom both on the plant and as a cut flower.

Disease resistance: Resistant to fusarium and virus tolerant as observed at Aurora, Oreg.

THE REPRODUCTIVE ORGANS

Stamens:

*Number.*—Six.

*Arrangement.*—Typical of genus Lilium.

*Anthers.*—Size: About 1.8 cm. Color: Red 59-B.

*Filaments.*—Length: About 5 cm. Color: Salmon 27-A.

*Pollen.*—Color: Greyed-Red 178-D.

Pistils:

*Number.*—1.

*Style.*—Length: About 3.5 to 4 cm. Color: Orange 28-C.

*Stigma.*—Color: Ruby Red 59-A.

Character of ovaries: Typical of the genus Lilium.

FRUIT

Fertility: The fruit is fertile.

Shape: Ovoid.

Color at maturity: Soft Brown.

This new variety most resembles the variety Impact, U.S. Plant Pat. No. 5,952.

I claim:

1. A new and distinct variety of Asiatic hybrid lily plant, substantially as herein shown and described, characterized by a generally Orange Buff coloration of the tepals each of which is brush marked with Ruby Red at the end of the nectary furrow; this plant blooming annually and profusely during the mid-season and growing with abundant foliage.

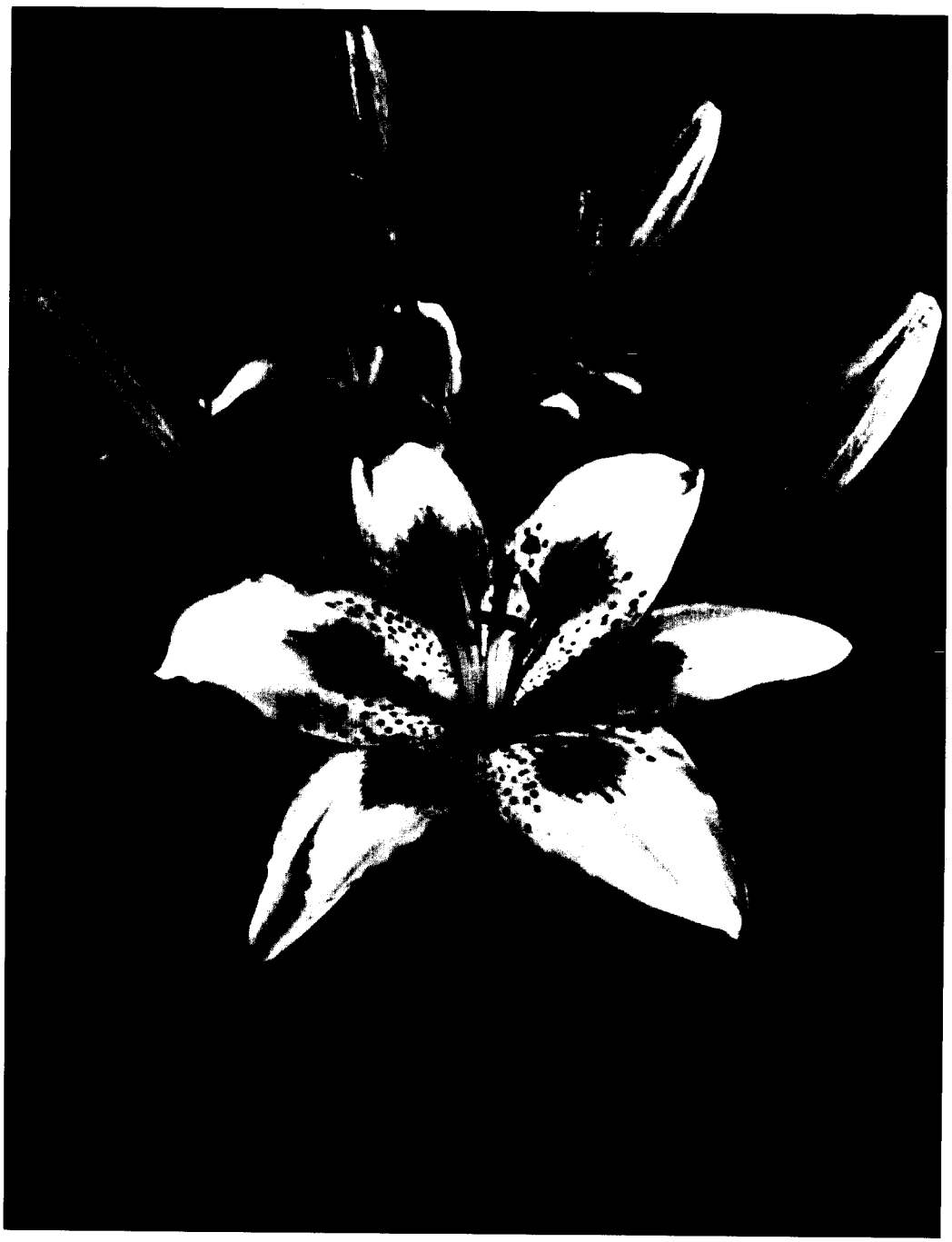

* * * * *